US008954075B2

(12) United States Patent
Paterson (10) Patent No.: US 8,954,075 B2
(45) Date of Patent: Feb. 10, 2015

(54) COMMUNICATIONS SYSTEM (75) Inventor: Robert Paterson, Tokyo (JP)

(73) Assignee: NEC Corporation, Tokyo (JP)

( * ) Notice: Subject to any disclaimer, the term of this patent is extended or adjusted under 35 U.S.C. 154(b) by 153 days.

(21) Appl. No.: 13/389,249

(22) PCT Filed: Aug. 10, 2010

(86) PCT No.: PCT/JP2010/063789
§ 371 (c)(1),
(2), (4) Date: Feb. 6, 2012

(87) PCT Pub. No.: WO2011/019083
PCT Pub. Date: Feb. 17, 2011

(65) Prior Publication Data
US 2012/0135739 A1 May 31, 2012

(30) Foreign Application Priority Data
Aug. 11, 2009 (GB) .................................. 0914024.5

(51) Int. Cl.
H04W 36/00 (2009.01)
C07K 14/195 (2006.01)
C12N 15/82 (2006.01)
H04W 36/14 (2009.01)
H04W 36/22 (2009.01)

(52) U.S. Cl.
CPC ......... *H04W 36/0094* (2013.01); *C07K 14/195* (2013.01); *C12N 15/8271* (2013.01); *C12N 15/8273* (2013.01); *H04W 36/14* (2013.01); *H04W 36/22* (2013.01)

USPC .......................... 455/436; 455/552.1; 370/331

(58) Field of Classification Search
USPC ........................... 455/436–444; 370/331, 332
See application file for complete search history.

(56) References Cited

U.S. PATENT DOCUMENTS 7,522,920 B2   4/2009  Hannu et al.
2006/0128394 A1  6/2006  Turina et al.

FOREIGN PATENT DOCUMENTS

| CN | 101080937 A | 11/2007 |
| CN | 101316400 A | 12/2008 |
| EP | 0 505 341 A2 | 9/1992 |
| JP | 2006-262178 A | 9/2006 |
| JP | 2007-503745 A | 2/2007 |
| WO | WO 2008/059994 A1 | 5/2008 |

OTHER PUBLICATIONS

International Search Report in PCT/JP2010/063789 dated May 5, 2011 (English Translation Thereof).

(Continued)

Primary Examiner — Vladimir Magloire
(74) Attorney, Agent, or Firm — McGinn IP Law Group, PLLC (57) ABSTRACT A mobile communications system is described in which an E-UTRAN base station dynamically changes its handover and/or its cell reselection parameters to control the load on the base station and which transmits a message to a non E-UTRAN neighboring cell, so that it can adapt its handover and/or its cell reselection parameters to avoid repeated handover and/or cell reselection of a mobile communications device between the non E-UTRAN cell and the E-UTRAN cell.

20 Claims, 4 Drawing Sheets (56) References Cited

OTHER PUBLICATIONS

NEC "Inter-RAT Load Balancing: E-UTRAN Parameter Optimization" 3GPP Draft; R3-091962, $3^{rd}$ Generation Partnership Project (3GPP), Mobile Competence Centre; 650, Route des Lucioles; F-06921 Sophia-Antipolis Cedex; France; No. Shenzhen, China; 20090820, Aug. 20, 2009, XP050353314 [retrieved on Aug. 20, 2009].

NEC "Inter-RAT Load Balancing: UTRAN Parameter Optimization" 3GPP Draft; R3-091963, $3^{rd}$ Project (3GPP), Mobile Competence Centre; 650, Route des Lucioles; F-06921 Sophia-Antipolis Cedex; France; No. Shenzhen, China; 20090820, Aug. 20, 2009, XP050353314 [retrieved on Aug. 20, 2009].

3GPP TS 36.331, V8.6.0. (Jun. 2009), Techincal Specification, $3^{rd}$ Generation Partnership Project; Technical Specification Group Radio Access Network; Evolved Universal Terrestrial Radio Access (E-UTRA) Radio Resource Control (RRC); Protocol Specification (Release 8).

3GPP TS 36.902, V1.2.0. (May 2009), Technical Report, $3^{rd}$ Generation Partnership Project; Techincal Specification Group Radio Access Network; Evolved Universal Terrestrial Radio Access (E-UTRA) Self-Configuring and Self-Optimizing Network Use Cases and Solutions (Release 9).

3GPP TS 32.102, V8.2.0. (Dec. 2008), Technical Specification, $3^{rd}$ Generation Partnership Project; Techincal Specification Group Services and System Aspects; Telecommunication management; Architecture (Release 8).

3GPP TS 36.304, V8.6.0. (Jun. 2009), Technical Specification, $3^{rd}$ Generation Partnership Project; Techincal Specification Group Radio Access Network; Evolved Universal Terrestrial Radio Access (E-UTRA) User Equipment (UE) procedures in idle mode (Release 8).

3GPP TS 25.331 V8.7.0. (Jun. 2009), Technical Specification, $3^{rd}$ Generation Partnership Project; Techincal Specification Group Radio Access Network; Radio Resource Control (RRC); Protocol Specification (Release 8).

3GPP TS 25.304 V8.6.0. (Jun. 2009), Technical Report, $3^{rd}$ Generation Partnership Project; Techincal Specification Group Radio Access Network; User Equipment (UE) procedures in idle mode and procedures for cell reselection in connected mode (Release 8).

Japanese Office Action dated Mar. 5, 2014, with partial English translation.

Chinese First Office Action dated Dec. 19, 2013, with English translation.

COMMUNICATIONS SYSTEM

FIELD OF THE INVENTION

The present invention relates to mobile telecommunication networks, particularly but not exclusively networks operating according to the 3GPP standards or equivalents or derivatives thereof. The invention has particular although not exclusive relevance to the Long Term Evolution (LTE) of UTRAN (called Evolved Universal Terrestrial Radio Access Network (E-UTRAN)) and its interaction with other networks such as UTRAN and GERAN (GSM EDGE Radio Access Network) networks.

BACKGROUND ART

In a cellular communications network, mobile devices or User Equipment (UE) roam from cell to cell as the user moves within the area covered by the cellular network. Generally, this roaming is governed by two processes—"handover" when the mobile device is in an active connected mode such as when the mobile device is in a call with another device; and "reselection" when the mobile device is in an idle mode or in a connected mode that does not have dedicated resources. In order to make a determination of which cell a UE should register with, at regular intervals the UE makes various measurements of signals received from different cells. Cell reselection is performed by the mobile device based on those measurements and cell reselection parameters provided by the serving cell. Handover, on the other hand is determined by the serving cell based on the measurements provided to it by the mobile device. The handover and cell reselection processes are based not only on the cell that has the strongest signal strength, but also on the services offered by the cell and hence the cell priority. For example, the strongest signal measured by the mobile device may be from a legacy GSM cell, yet the mobile device may select a higher priority E-UTRAN cell provided its signal strength is sufficient to provide an adequate service.

DISCLOSURE OF THE INVENTION

Problems to be Solved

A problem with these handover and cell reselection processes is that they can lead to some cells being fully utilised whilst other cells are underutilised. This problem is addressed by performing load balancing to share scarcely available radio resources and the processing load between the available base station cells. A recent proposal for E-UTRAN base station cells is to control the load balancing by dynamically changing handover and cell reselection parameters provided to the mobile devices. Thus, if a high priority E-UTRAN cell determines that it is providing service to too many mobile devices it can change the handover and/or the cell reselection parameters that it transmits, making it more likely that mobile devices located towards the edge of the cell will select a different cell with which to register.

The inventors have realised, however, that if the mobile device moves to a cell of a different Radio Access Technology (RAT), the handover and cell reselection parameters of the new cell may cause the mobile device to select the E-UTRAN cell again, thereby causing the mobile device to "ping-pong" between the E-UTRAN cell and the other cell.

Means for Solving the Problems

Embodiments of the present invention aim to provide techniques for controlling handover and/or cell reselection parameters used by cells of different RATs to allow efficient load balancing to be performed.

According to one aspect, the present invention provides a method performed by an E-UTRAN communications system comprising: generating a message for a neighbouring cell of a different Radio Access Technology, RAT, the message including information for use in determining new handover and/or cell reselection parameters for the neighbouring cell of the other RAT for reducing the repeated handover and/or reselection of a mobile communications device between the E-UTRAN cell and the cell of the other RAT; and sending the message to the cell of the other RAT. The message can be generated in response to the generation of new handover and/or cell reselection parameters of the E-UTRAN cell that are determined in order to control the loading on the E-UTRAN cell.

The message may be generated prior to or after the E-UTRAN system changes its own handover and/or cell reselection parameters.

The method may be performed by the E-UTRAN base station or by a Telecommunications Management Network (see TS 32.102 V8.2.0).

In order to control the load on the E-UTRAN cell, the cell may change the thresholds that it broadcasts into the cell. Hysteresis parameters could be varied as well as or instead of varying the thresholds. The threshold values that are changed can include one or more of: a threshold used to detect when the mobile device should consider other cells to which to handover: a threshold used to define a low signal quality from the serving cell.

The message that is sent to the other RAT may include new handover and/or cell reselection parameters that the other RAT should use. Alternatively, the message may identify the changes that the E-UTRAN cell has made or will make to its handover and/or cell reselection parameters.

The present invention also provides a method performed by a non E-UTRAN cell, the method comprising: transmitting handover and/or cell reselection parameters for use by mobile telecommunications devices to control signal measurements performed thereby as part of a handover and/or cell reselection process; receiving a message from an E-UTRAN communications node, the message including information for use in determining new handover and/or cell reselection parameters for the non E-UTRAN cell for reducing repeated handover and/or cell reselection of a mobile communications device between an E-UTRAN cell and the non E-UTRAN cell; and transmitting the new handover and/or cell reselection parameters into the non-E-UTRAN cell.

According to another aspect, the present invention provides an E-UTRAN communications system comprising: means for generating a message for a neighbouring cell of a different Radio Access Technology, RAT, the message including information for use in determining new handover and/or cell reselection parameters for the neighbouring cell of the other RAT for reducing the repeated handover and/or cell reselection of a mobile communications device between the E-UTRAN cell and the cell of the other RAT; and means for sending the message to the cell of the other RAT.

According to another aspect, the present invention provides an E-UTRAN communications node comprising: a load balancing module operable: i) to change handover and/or cell reselection parameters of the E-UTRAN cell; ii) to provide a message for a neighbouring cell of a different Radio Access Technology, RAT, the message including information for use in determining new handover and/or cell reselection parameters for the neighbouring cell of the other RAT for reducing the repeated handover and/or cell reselection of a mobile communications device between the E-UTRAN cell and the cell of the other RAT; and iii) to send the message to the cell of the other RAT.

According to another aspect, the present invention provides a non E-UTRAN cell comprising: transmission circuitry for transmitting handover and/or cell reselection parameters for use by mobile telecommunications devices to control signal measurements performed thereby as part of a handover and/or cell reselection process; receiving circuitry for receiving a message from an E-UTRAN communications node, the message including information for use in determining new handover and/or cell reselection parameters for the non E-UTRAN cell for reducing repeated handover and/or cell reselection of a mobile communications device between an E-UTRAN cell and the non E-UTRAN cell; and wherein said transmission circuitry is operable to trans the new handover and/or cell reselection parameters into the non-E-UTRAN cell.

According to another aspect, the present invention provides a communications system comprising: a mobile communications device, an E-UTRAN communications system and a non-E-UTRAN communications system, wherein the E-UTRAN communications system is operable: i) to provide a message for a neighbouring cell of a different Radio Access Technology, RAT, the message including information for use in determining new handover and/or cell selection parameters for the neighbouring cell of the non E-UTRAN cell for reducing the repeated handover or cell reselection of a mobile communications device between the E-UTRAN cell and the non E-UTRAN cell; and ii) to send the message to the cell of the non E-UTRAN cell; wherein the mobile communications device is operable to make signal measurements in accordance with handover and/or cell reselection parameters broadcast by a serving cell; and wherein the non E-UTRAN cell comprises: transmission circuitry for transmitting cell selection parameters for use by mobile telecommunications devices to control signal measurements performed thereby as part of a handover and/or cell reselection process; receiving circuitry for receiving a message from the E-UTRAN communications system, the message including information for use in determining new handover and/or cell reselection parameters for the non E-UTRAN cell for reducing repeated handover and/or cell reselection of a mobile communications device between an E-UTRAN cell and the non E-UTRAN cell; and wherein said transmission circuitry is operable to transmit the new cell selection parameters into the non-E-UTRAN cell.

BRIEF DESCRIPTION OF THE DRAWINGS

These and other features and aspects of the invention will become apparent from the following detailed description of exemplary embodiments, that are described with reference to the accompanying drawings in which.

BEST MODE FOR CARRYING OUT THE INVENTION

Overview

Figure 1:
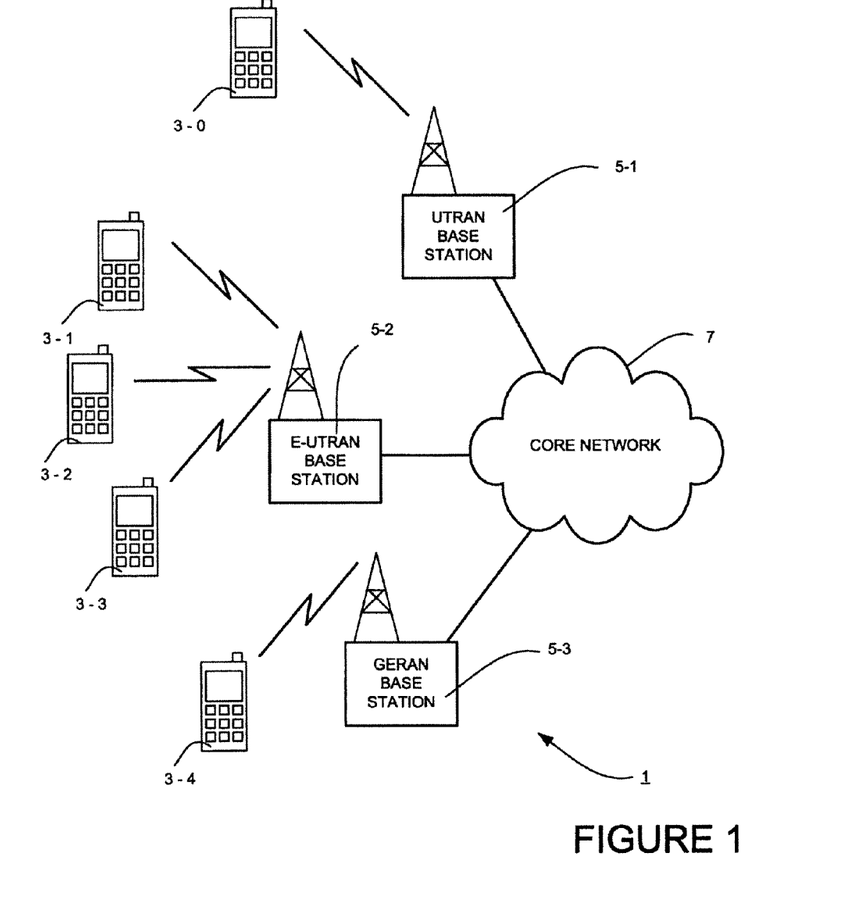
FIG. 1 schematically illustrates a mobile telecommunication system of a type to which the embodiment is applicable.

FIG. 1 schematically illustrates a mobile (cellular) telecommunication system 1 in which users of mobile telephones 3-0, 3-1, 3-2, 3-3 and 3-4 can communicate with other users (not shown) via one of the base stations 5-1, 5-2 or 5-3 and a telephone core network 7. In the system illustrated in FIG. 1, the base station 5-1 is a UTRAN base station and it is currently serving mobile telephone 3-0; base station 5-2 is an E-UTRAN base station and it is currently serving mobile telephones 3-1, 3-2 and 3-3; and base station 5-3 is a GERAN base station and it is currently serving mobile telephone 3-4. Each base station 5 operates a number of base station cells, each having a number of uplink and downlink communications resources (sub-carriers, time slots etc) that are available for wireless communication between the mobile telephones 3 and the corresponding base station 5. In this embodiment, it will be assumed for the sake of simplicity of explanation, that each base station 5 operates a single cell. The base stations 5 allocate downlink resources to each mobile telephone 3 depending on the amount of data to be sent to the mobile telephone 3. Similarly, the base stations 5 allocate uplink resources to each mobile telephone 3 depending on the amount and type of data the mobile telephone 3 has to send to the base station 5.

Each of the base stations 5 transmits handover parameters and cell reselection parameters and rules to be used by the mobile telephones 3 in making signal measurements of neighbouring cells and in the case of cell reselection for reselecting an available base station cell with which to register. The E-UTRAN base station 5-2 is part of a Self Organising Network (SON) that can adapt (change), among other things, the handover and/or cell reselection parameters that it transmits depending on its current status and load conditions. Typically, the E-UTRAN base station 5-2 will also communicate with its neighbouring base stations so that it is aware of the loading on the neighbouring base stations as well before deciding on whether or not it should change its handover and/or cell reselection parameters. If the handover and/or cell reselection parameters are changed by the E-UTRAN base station 5-2, then a mobile telephone 3 being served by the E-UTRAN base station 5-2 may reselect or handover to the UTRAN base station 5-1 or the GERAN base station 5-3. However, once this transfer to the UTRAN base station 5-1 or the GERAN base station 5-3 has been completed, the handover and/or cell reselection parameters and rules of the new base station may result in the mobile telephone 3 immediately returning to the E-UTRAN base station 5-2.

Therefore, in this embodiment when the E-UTRAN base station 5-2 decides to change its handover and/or cell reselection parameters, it informs its neighbouring base stations of different RATs (eg UTRAN base station 5-1 and GERAN base station 5-3) of the changes so that they can also change some of their handover and/or cell reselection parameters they transmit in order to reduce the likelihood of the mobile telephone ping-ponging between the E-UTRAN base station 5-2 and the UTRAN or GERAN base stations 5-1, 5-3. In one embodiment, the E-UTRAN base station 5-3 sends the UTRAN and/or the GERAN base station 5-1, 5-3 modified handover and/or cell reselection parameter values that it/they should transmit and in another embodiment, the E-UTRAN base station 5-2 simply informs the UTRAN and/or the GERAN base station 5-1, 5-3 of the changes that it has made—and then leaves it up to the UTRAN and/or the GERAN base station 5-1, 5-3 to make its own changes to its handover and/or cell reselection parameters.

E-UTRAN Base Station

Figure 2:
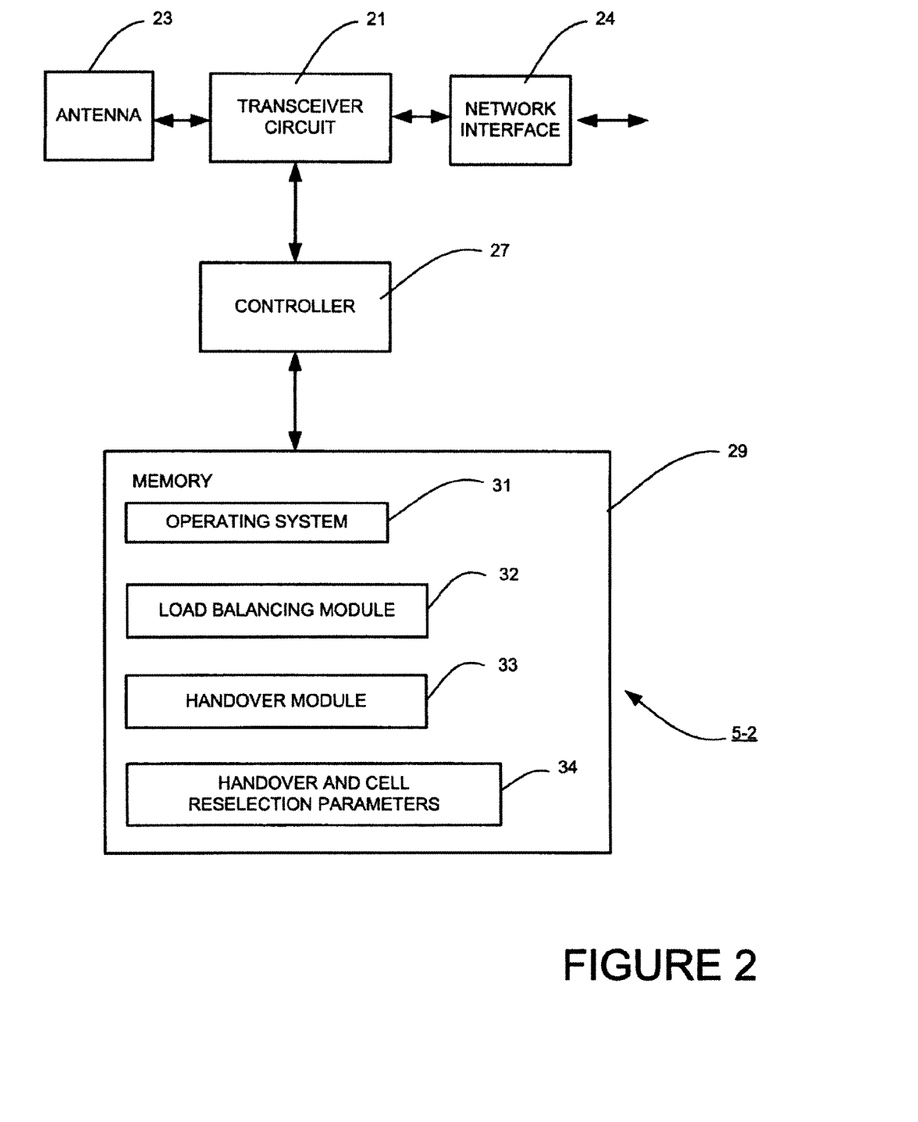
FIG. 2 schematically illustrates an E-UTRAN base station forming part of the system shown in FIG. 1.

FIG. 2 is a block diagram illustrating the main components of the E-UTRAN base station 5-2 used in this embodiment. As shown, the E-UTRAN base station 5-2 includes a transceiver circuit 21 which is operable to transmit signals to and to receive signals from the mobile telephones 3 via one or more antennae 23 and to transmit signals to and receive signals from the telephone core network 7 via the interface 24. A controller 27 controls the operation of the transceiver circuit 21 in accordance with software and data stored in memory 29. The software and data includes, among other things, an operating system 31, a load balancing module 32, a handover module 33 and handover and cell reselection parameters 34. The load balancing module 32 is operable to decide whether or not load balancing is needed (based on its own loading as well as on the loading of the neighbouring base stations) and, if so, to change its handover and cell reselection parameters 34 that it transmits within its cell via the antenna 23. In this embodiment, the load balancing module 32 is also operable to inform neighbouring UTRAN and/or GERAN base stations 5-1, 5-3 (via the core network 7) of the changes that it will make (or has made) to its handover and cell reselection parameters 34 or to inform them of changes that they should make to their handover and cell reselection parameters. The Handover module 33 is responsible for controlling handover of mobile telephones 3 to or from the E-UTRAN base station 5-2.

UTRAN Base Station

Figure 3:
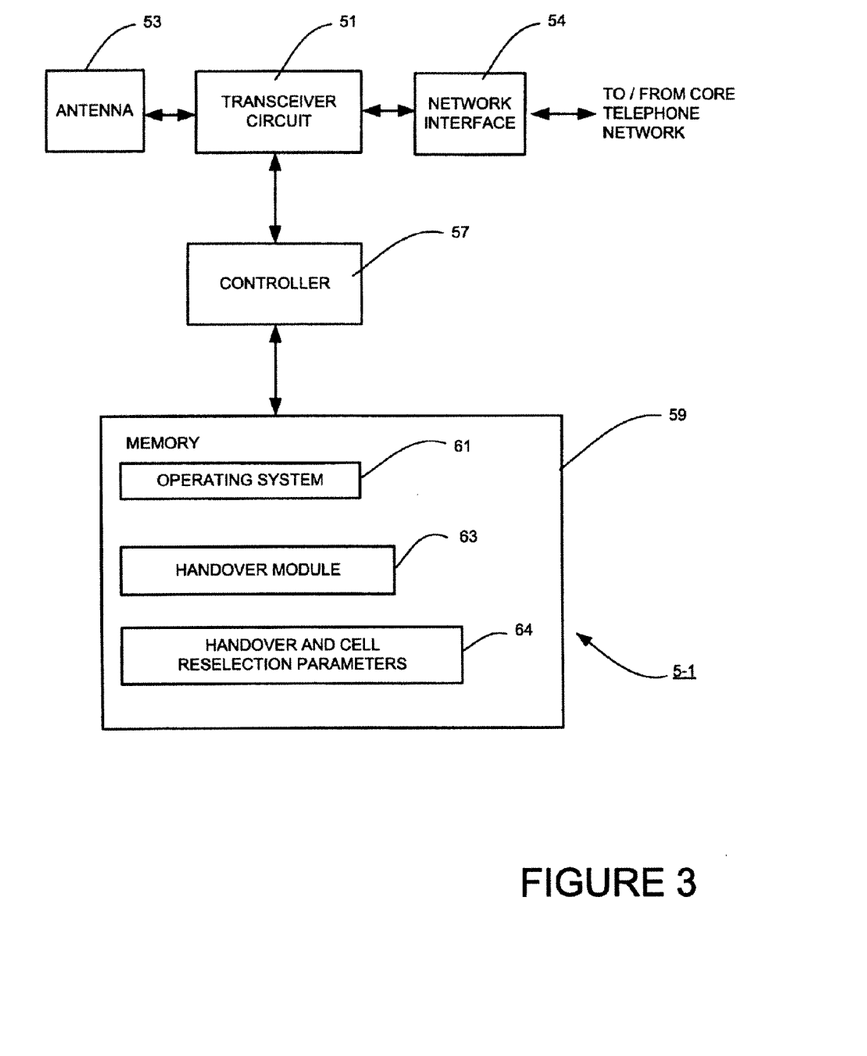
FIG. 3 schematically illustrates a UTRAN base station forming part of the system shown in FIG. 1.

FIG. 3 is a block diagram illustrating the main components of the UTRAN base station 5-1 used in this embodiment. The GERAN base station 5-3 will have a similar structure. As shown, the UTRAN base station 5-1 includes a transceiver circuit 51 which is operable to transmit signals to and to receive signals from the mobile telephones 3 via one or more antennae 53 and to transmit signals to and receive signals from the telephone core network 7 via the interface 54. A controller 57 controls the operation of the transceiver circuit 51 in accordance with software and data stored in memory 59. The software and data includes, among other things, an operating system 61, a handover module 63 and handover and cell reselection parameters 64. The handover module 63 is responsible for transmitting the handover and cell reselection parameters and for controlling handover of mobile telephones 3 to or from the UTRAN base station 5-1. In this embodiment, the handover module 63 receives notifications from neighbouring E-UTRAN base stations 5-2 (via the core network 7) of changes that should be made to the handover and/or cell reselection parameters 64 and makes these changes accordingly. In an alternative embodiment, the handover module 63 may receive notifications of changes that the E-UTRAN base station 5-2 has made or will make to its handover and/or cell reselection parameters 34 and, in response, may calculate appropriate changes that it should make to its handover and/or cell reselection parameters 64 in order to reduce the above described "ping-pong" problem.

In the above description, the base stations 5 are described for ease of understanding as having a number of discrete modules (such as the load balancing modules and the handover modules). Whilst these modules may be provided in this way for certain applications, for example where an existing system has been modified to implement the invention, in other applications, for example in systems designed with the inventive features in mind from the outset, these modules may be built into the overall operating system or code and so these modules may not be discernible as discrete entities.

Mobile Telephone

Figure 4:
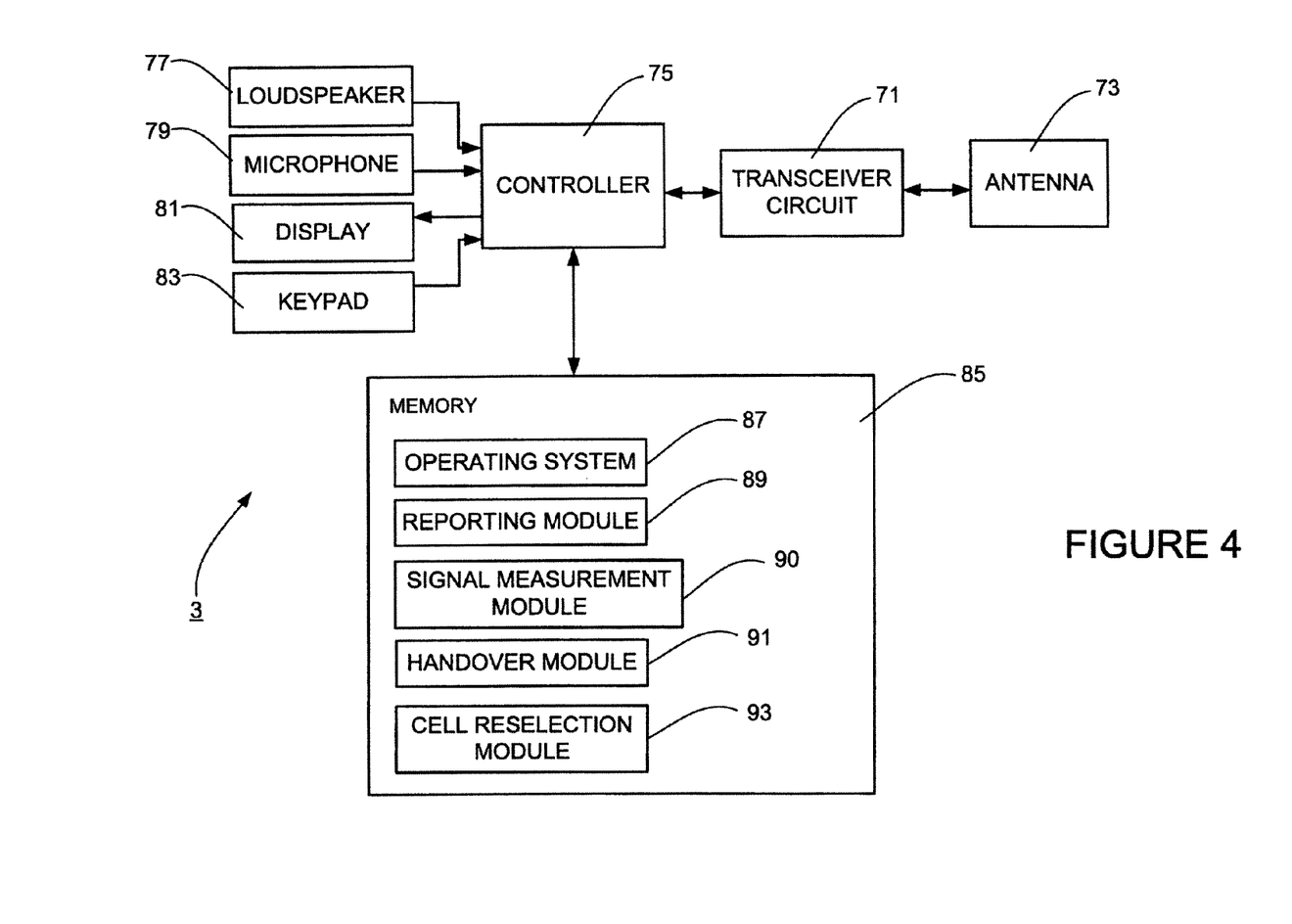
FIG. 4 schematically illustrates a mobile telephone forming part of the system shown in FIG. 1.

FIG. 4 schematically illustrates the main components of each mobile telephone 3 shown in FIG. 1. As shown, the mobile telephone 3 includes transceiver circuitry 71 which is operable to transmit signals to and to receive signals from the base station 5 via one or more antennae 73. As shown, the mobile telephone 3 also includes a controller 75 which controls the operation of the mobile telephone 3 and which is connected to the transceiver circuit 71 and to a loudspeaker 77, a microphone 79, a display 81, and a keypad 83. The controller 27 operates in accordance with software instructions stored within memory 85. As shown, these software instructions include, among other things, an operating system 87, a reporting module 89, a signal measurement module 90, a handover module 91 and a cell reselection module 93.

In this embodiment: the signal measurement module 90 is operable to make measurements on signals received from cells within range of the mobile telephone 3 and in accordance with handover or cell reselection parameters received from the base station 5 with which the mobile telephone 3 is currently registered. The reporting module is operable to report the occurrence of specified events back to the serving base station 5. The handover module 91 is operable to control the handover of the mobile telephone 3 from one cell to another and the cell reselection module 93 is operable to control cell reselection.

Handover and Cell Reselection Parameters

E-UTRAN Base Station

There are a number of different handover and cell reselection parameters that can be changed by the E-UTRAN base station 5-2 in order to perform load balancing—by delaying or advancing the time that some mobile telephones 3 will handover to or reselect the cell of another RAT. The following is given by way of example.

When the mobile telephone 3 is in a connected mode, a typical sequence of events for inter-RAT mobility is:

1. The E-UTRAN base station 5-2 configures a mobile telephone 3 to report when the measurement for the serving cell becomes worse than a first threshold (defined in TS 36.331 V8.6.0 as Event A2).
2. Upon receipt of an event A2 measurement report from a mobile telephone 3, the E-UTRAN base station 5-2 configures the mobile telephone 3 to report when the measurement for the serving cell becomes worse than (lower than) a second threshold (lower than the first threshold) and the measurement for a neighbouring cell (of a different RAT) is better than a third threshold (defined in TS 36.331 V8.6.0 as Event B2).
3. Upon reception of an event B2 measurement report from the mobile telephone 3, the E-UTRAN base station 5-2 commences an inter-RAT handover to the neighbouring cell.

Event A2 is defined in TS 36.331 V8.6.0 as follows:

$$Ms + Hys < Thresh$$

where:

Ms is the measurement result of the serving cell, not taking into account any offsets.

Hys is the hysteresis parameter for this event (i.e. hysteresis as defined within reportCofigEUTRA for this event).

Thresh is the threshold parameter for this event (i.e. a2-Threshold as defined within reportConfigEUTRA for this event).

Event B2 is defined in TS 36.331 V8.6.0 as follows:

$$Ms + Hys < Thresh\ 1 \qquad \text{Inequality B2-1 (Condition 1)}$$

$$Mn + Ofn - Hys > Thresh\ 2 \qquad \text{Inequality B2-2 (Condition 2)}$$

The variables in the formula are defined as follows:

Ms is the measurement result of the serving cell, not taking into account any offsets.

Mn is the measurement result of the inter-RAT neighbour cell, not taking into account any offsets.

Ofn is the frequency specific offset of the frequency of the inter-RAT neighbour cell (i.e. offsetFreq as defined within the measObject corresponding to the frequency of the inter-RAT neighbour cell).

Hys is the hysteresis parameter for this event (i.e. hysteresis as defined within reortConfigInterRAT for this event).

Thresh1 is the threshold parameter for this event (i.e. b2-Threshold1 as defined within reportConfigInterRAT for this event).

Thresh2 is the threshold parameter for this event (i.e. b2-Threshold2 as defined within reportConfigInterRAT for this event).

The thresholds are part of the handover and cell reselection parameters 34 that are transmitted by the E-UTRAN base station 5-2. By varying the thresholds that the mobile telephones 3 use when making these measurements, the E-UTRAN base station 5-2 can cause the reporting of events A2 and B2 to be reported earlier or later depending on how the thresholds are changed. Therefore, if the load balancing module 32 determines that the E-UTRAN base station 5-2 is under-utilised, then it can lower the threshold, Thresh, used to detect Event A2 and/or it can lower the threshold, Thresh1, used to detect Event B2. This will cause the mobile telephones 3 to detect the event later than they would have done—thereby causing the mobile telephones 3 to remain with the E-UTRAN base station 5-2 for longer. Similarly, if the load balancing module 32 determines that the E-UTRAN base station 5-2 is over-utilised, then it can increase the threshold, Thresh, used to detect Event A2 and/or it can increase the threshold, Thresh1, used to detect Event B2. This will cause the mobile telephone 3 to detect the event earlier than it would have done—thereby causing the handover of the mobile telephone 3 to happen more quickly, which in turn reduces the load on the E-UTRAN base station 5-2.

When the mobile telephone 3 is in an idle mode, the mobile telephone makes its own decision about the cell with which it will register. If it is assumed that typically the absolute priority of E-UTRAN cells will be higher than the absolute priority of other RAT cells (eg UTRAN and GERAN cells), then the cell reselection criteria from E-UTRAN to another RAT are very similar to event B2 in connected mode discussed above.

In particular, TS 36.304 V8.6.0 defines that when a mobile telephone 3 is camping on a higher priority frequency, cell reselection is performed when the quality of the target cell is above a certain threshold and the quality of the serving cell is below another threshold, as follows:

$S_{ServingCell} < \text{Thresh}_{serving, low}$ and the $S_{nonServingCell,x}$ of a cell of a lower priority frequency is greater than $\text{Thresh}_{x, low}$ during a time interval $\text{Treselection}_{RAT}$; and The mobile telephone has camped on the current serving cell for more than 1 second.

Where $S_{ServingCell}$ is the quality of the serving cell (which depends on the strength of the signal received from the serving cell) and $S_{nonServingCell,x}$ is the quality of the target cell.

Therefore, again the load on the E-UTRAN base station 5-2 can be controlled by varying the threshold $\text{Thresh}_{serving, low}$, in the manner discussed above. As those skilled in the art will appreciate, the threshold $\text{Thresh}_{serving, low}$, is one of the cell reselection parameters 34 that the E-UTRAN base station broadcasts within its cell.

UTRAN Base Station

3GPP standards documentation TS 25.331 V8.7.0 defines the triggers that cause a mobile telephone 3 to transfer from a UTRAN cell to another cell when in the connected and idle modes. The inventors assume that event 3C will be used as the trigger for handover of a mobile telephone 3 in connected mode from a UTRAN cell to an E-UTRAN cell (eg from UTRAN base station 5-1 to E-UTRAN base station 5-2). Under event 3C, a mobile telephone 3 will handover to a higher priority cell of another RAT if the following condition is met:

$$M_{Other\ RAT} + CIO_{Other\ RAT} \geq T_{Other\ RAT} + H_{3c}/2$$

where:

$M_{Other\ RAT}$ is the measurement quantity for the cell of the other system. $M_{Other\ RAT}$ is expressed in dBm.

$CIO_{Other\ RAT}$ is the cell individual offset for the cell of the other system.

$T_{Other\ RAT}$ is the absolute threshold that applies for the other system in that measurement.

$H_{3c}$ is a hysteresis parameter for event 3c.

(At present the parameter $CIO_{Other\ RAT}$ is not defined for E-UTRAN cells.)

In order to reduce the chances of a mobile telephone 3 being repeatedly transferred between the UTRAN cell and the E-UTRAN cell as a result of the dynamic changes of the handover and/or cell reselection parameters performed by the E-UTRAN base station 5-2, the present embodiment proposes that the value of the threshold $T_{Other\ RAT}$ used by the UTRAN cell is modified in a complementary way to the way in which the threshold values in the E-UTRAN cell are modified. Thus if the thresholds used in the E-UTRAN base station 5-2 are changed to reduce the load on the E-UTRAN base station 5-2 then, in the UTRAN base station 5-1, the threshold $T_{Other\ RAT}$ should be increased so that there will be a delay before mobile telephones 3 will handover to the E-UTRAN base station 5-2—which in turn helps to reduce the load on the E-UTRAN base station 5-2. Similarly, if it is desired to increase the load on the E-UTRAN base station 5-2, then the threshold $T_{Other\ RAT}$ should be decreased so that handover of mobile telephones 3 from the UTRAN base station 5-1 to the E-UTRAN base station 5-1 will happen more quickly than before.

Similarly, for mobile telephones 3 that are in an Idle mode, the inventors assume that the mobile telephone 3 when camping on a UTRAN or GERAN cell will reselect the E-UTRAN cell if the quality of the signal broadcast by the E-UTRAN cell (as received by the mobile telephone 3) is greater than a threshold value (such as threshold $\text{Thresh}_{x,high}$). If it is, then the mobile telephone 3 will camp on the E-UTRAN cell. Therefore by varying this threshold value in a complementary way to the way that the threshold value $\text{Thresh}_{x,low}$ is changed by the E-UTRAN base station 5-2, the problem of mobile telephones 3 being repeatedly transferred between the E-UTRAN cell and the UTRAN cell is at least reduced.

At present, the handover and cell reselection parameters used in UTRAN and GERAN base stations 5-1, 5-3 are fixed and no mechanism is provided in the base stations that will allow them to calculate new values based on load measurements. The inventors propose, therefore, that the E-UTRAN base station 5-2 sends a message to the neighbouring UTRAN and GERAN base stations 5-1 and 5-3 to allow them to change their cell selection/reselection parameters in line with the changes made by the E-UTRAN base station 5-1.

In one embodiment, the E-UTRAN base station 5-1 calculates new threshold values to be used by the GERAN and UTRAN base stations 5-1 and 5-3 (such as $T_{Other\ RAT}$) and sends these to the neighbouring UTRAN and GERAN base stations 5-1 and 5-3. The messages will be sent via the core network 7 using appropriate S1AP and RANAP messages, such as the DIRECT INFORMATION TRANSFER message. In response to receiving such a message, the UTRAN and GERAN base stations 5-1, 5-3 will extract the new threshold value(s) from the message and update their handover and cell reselection parameters accordingly so that the new values will be transmitted to the mobile telephones 3 that those base stations are serving.

In another embodiment, the E-UTRAN base station 5-1 reports the changes that it makes to its own threshold values to the GERAN and UTRAN base stations 5-1 and 5-3, which in turn work out corresponding changes to make to their own cell selection/reselection parameters. For example, the E-UTRAN base station may send all of its neighbouring base stations details of the changes that it has made or will make to the threshold values it uses to detect events A2 and B2 and details of changes to $Thresh_{x, low}$. In response, the UTRAN base station 5-1 and the GERAN base station 5-3 can make appropriate changes to the thresholds they use for controlling transfer of mobile telephones 3 from the UTRAN/GERAN cell to the E-UTRAN cell to try to avoid the above described "ping pong" problem. For example, the UTRAN base station 5-1 could just set the value of $T_{Other\ RAT}$ to the same value as the threshold Thresh1 used to detect event B2 by mobile telephones 3 being served by the E-UTRAN base station 5-2.

Modifications and Alternatives

A detailed embodiment has been described above. As those skilled in the art will appreciate, a number of modifications and alternatives can be made to the above embodiment whilst still benefiting from the inventions embodied therein.

In the above embodiment, a mobile telephone based telecommunications system was described. As those skilled in the art will appreciate, the signalling and handover techniques described in the present application can be employed in other communications system. Other communications nodes or devices may include user devices such as, for example, personal digital assistants, laptop computers, web browsers, etc.

In the above embodiments, a number of software modules were described. As those skilled will appreciate, the software modules may be provided in compiled or un-compiled form and may be supplied to the base stations or to the mobile telephone as a signal over a computer network, or on a recording medium. Further, the functionality performed by part or all of this software may be performed using one or more dedicated hardware circuits. However, the use of software modules is preferred as it facilitates the updating of base station 5 and the mobile telephones 3 in order to update their functionalities.

In the above embodiment, the thresholds were changed to control the load on the E-UTRAN base station. The same result can be achieved by varying the hysteresis parameters that are part of the measurements performed by the mobile telephones. This can be done instead of varying the threshold values or in addition to varying the threshold values.

In the above embodiment, the E-UTRAN base station 5-2 changed both its handover and cell reselection parameters to control its loading. In an alternative embodiment, only the handover parameters or only the cell reselection parameters may be changed to control its loading.

In the above embodiments, the handover and/or the cell reselection parameters were changed in order to control the load on the E-UTRAN cell. However, the handover and/or the cell reselection parameters may be changed by the E-UTRAN cell for other reasons and in this case, messages may still be transmitted to the neighbouring UTRAN and GERAN base stations so that they can change their handover and/or cell reselection parameters to avoid the above ping-pang problem.

In the above embodiment, the E-UTRAN base station monitored its loading and adapted its cell selection/reselection parameters accordingly. In another embodiment, a node within a Telecommunications Management Network may monitor the load on the E-UTRAN base station 5-2 and perhaps also the load on the neighbouring UTRAN and GERAN base stations 5-1 and 5-3. This management network node may then inform the E-UTRAN base station 5-2 of new cell selection/reselection parameters (or at least the need to increase or decrease the load, which the E-UTRAN base station uses to work out its own new handover and/or cell reselection parameters). Similarly, this management network node may also inform the UTRAN and GERAN cells of the new handover and/or cell reselection parameters that they should use or of those for the E-UTRAN base station so that they can calculate their own new parameters accordingly. As a further alternative, the E-UTRAN base station may determine its own loading and then report this to the management network node. This management network node may then use the reported loading information to decide on new handover and/or cell reselection parameters for a number of neighbouring base stations which it then distributes to those base stations.

Various other modifications will be apparent to those skilled in the art and will not be described in further detail here.

GLOSSARY OF 3GPP TERMS

LTE—Long Term Evolution (of UTRAN)
UE—User Equipment—mobile communication device
DL—downlink—link from base to mobile
UL—uplink—link from mobile to base
MME—Mobility Management Entity
UPE—User Plane Entity
HO—Handover
RLC—Radio Link Control
RRC—Radio Resource Control
UTRAN—Universal Terrestrial Radio Access Network
GERAN—GSM/Edge Radio Access Network The following is a detailed description of the way in which the present inventions may be implemented in the currently proposed 3GPP standards. Whilst various features are described as being essential or necessary, this may only be the case for the proposed 3GPP standard, for example due to other requirements imposed by the standard. These statements should not, therefore, be construed as limiting the present invention in any way.

Introduction

Currently, [1] lists the frequency specific offset parameter as the candidate parameter for optimization in the Inter-RAT Load Balancing use case. A proposal to optimize different E-UTRAN parameters can be found in reference [2].

This contribution proposes a mechanism to optimize UTRAN parameters.

Discussion

It is proposed in [2] to optimize the following inter-RAT measurement parameters for SON Inter-RAT load balancing:

Thresh of event A2
Thresh 1 of event B2
$Thresh_{serving,\ low}$.

The effect of modifying these parameters is to advance or delay handover from LTE to other RATs. To avoid ping-pong effects, there should be an equivalent modification of handover parameters in other RATs to delay or advance handover from the other RAT to LTE.

UTRAN to LTE HO

It is assumed that the event 3C (defined in [3]) would be used as the trigger for handover from UTRAN to LTE. When the quality of the LTE cell rises above a threshold, handover is triggered.

Event 3C is defined in [3] as follows:

$$M_{Other\ RAT} + CIO_{Other\ RAT} \geq T_{Other\ RAT} + H_{3c}/2$$

The variables in the formula are defined as follows:

$M_{Other\ RAT}$ is the measurement quantity for the cell of the other system. $M_{Other\ RAT}$ is expressed in dBm.

$CIO_{Other\ RAT}$ is the cell individual offset for the cell of the other system.

$T_{Other\ RAT}$ is the absolute threshold that applies for the other system in that measurement.

$H_{3c}$ is the hysteresis parameter for event 3c.

It should be noted that the parameter $CIO_{Other\ RAT}$ is not defined for LTE cells.

To align with the proposal in [2], the appropriate parameter to optimize is $T_{Other\ RAT}$.

UTRAN to LTE Cell Reselection

To complement the proposed optimization of $Thresh_{serving,\ low}$ as proposed in [2], it is additionally proposed to optimize $Thresh_{x,high}$ for the UTRAN to LTE cell reselection case. As in [2], this assumes that LTE frequencies are given a higher absolute priority than UTRAN frequencies.

See [4] for the details of the cell reselection algorithm.

Parameter Negotiation

It is necessary to define a mechanism by which measurement parameters of other RATs are optimized by E-UTRAN. There are two options:
1. The E-UTRAN node determine the values of $T_{Other\ RAT}$ and $Thresh_{x,high}$ which UTRAN should apply
2. The E-UTRAN node informs UTRAN of the values of Thresh (of event A2), Thresh 1 (of event B2) and $Thresh_{serving,\ low}$ which E-UTRAN is intending to apply. As a result UTRAN can apply an appropriate value to $T_{other\ RAT}$ and $Thresh_{x,high}$ in order to avoid ping-pong.

A new procedure to negotiate a new value of $T_{Other\ RAT}$ should be introduced. The signalling can re-use the following S1AP and RANAP messages:

S1AP: eNB DIRECT INFORMATION TRANSFER
S1AP: MME DIRECT INFORMATION TRANSFER
RANAP: DIRECT INFORMATION TRANSFER

In case option 2 above is preferred, after receives the threshold values applied in E-UTRAN, UTRAN can consider that $T_{Other\ RAT}$ should be set to the same as Thresh1 of event B2. Ping-pong is avoided by setting of hysteresis parameters in both event 3c and event B2.

Proposal
TBD
Conclusion
TBD

REFERENCES

[1] TR 36.902, VL 2.0. Self-configuring and self-optimizing network use cases and solutions (Release 9)
[2] R3-091962 IRAT MLB Parameter Optimization (NEC)
[3] TS 25.331 Radio Resource Control (RRC)
[4] TS 25.304, V8.6.0 User Equipment (UE) procedures in idle mode This application is based upon and claims the benefit of priority from United Kingdom Patent Application No. 0914024.5, filed on Aug. 11, 2009, the disclosure of which is incorporated herein in its entirety by reference.

The invention claimed is:

1. A method performed by a communications node of an E-UTRAN (Evolved Universal Terrestrial Radio Access Network) communications system, the method comprising:
changing handover and/or cell reselection parameters of an E-UTRAN cell;
generating a message for a neighboring cell of a different Radio Access Technology (RAT), another RAT, the message including at least one handover and/or cell reselection parameter for use in determining new handover and/or cell reselection parameters for the neighboring cell of the other RAT; and
sending the message to a base station operating the neighboring cell of the other RAT.

2. The method according to claim 1, wherein the generating and sending are performed prior to the changing.

3. The method according to claim 1, performed by a E-UTRAN cell.

4. The method according to claim 1, wherein said changing changes the threshold values transmitted by the cell that are used by mobile communications devices to control measurements performed by the mobile communications devices as part of a handover or cell reselection process.

5. The method according to claim 4, wherein said threshold values that are changed include one or more of: a threshold used to detect when the mobile device should consider other cells to which to handover; and a threshold used to define a low signal quality for the serving cell.

6. The method according to claim 1, wherein the at least one handover and/or cell reselection parameter included in the message comprises the new handover and/or cell selection parameters for the other RAT cell.

7. The method according to claim 1, wherein the at least one handover and/or cell reselection parameter included in the message comprises data identifying the changes made to the handover and/or cell reselection parameters of the E-UTRAN cell.

8. A method performed by a base station of a non E-UTRAN (Evolved Universal Terrestrial Radio Access Network) cell, the method comprising:
transmitting handover and/or cell reselection parameters for use by mobile communications devices to control signal measurements performed thereby as part of a handover and/or cell reselection process;
receiving a message from an E-UTRAN communications node, the message including at least one handover and/or cell reselection parameter for use in determining new handover and/or cell reselection parameters for the non E-UTRAN cell;
determining, from said at least one handover and/or cell reselection parameter, said new handover and/or cell reselection parameters for the non E-UTRAN cell; and
transmitting the new handover and/or cell reselection parameters into the non-E-UTRAN cell for use by mobile communications devices to control signal measurements performed thereby as part of a handover and/or cell reselection process.

9. The method according to claim 8, wherein the at least one handover and/or cell reselection parameter included in the message comprise the new handover and/or cell reselection parameters for the non E-UTRAN cell.

10. The method according to claim 8, wherein the at least one handover and/or cell reselection parameter included in the message comprise data identifying changes made to the handover and/or cell reselection parameters of the E-UTRAN cell.

11. The method according to claim 8, wherein the message is received from the E-UTRAN communications node via the core network.

12. A communications node of a communications system comprising:
- means for changing handover and/or cell reselection parameters of an E-UTRAN (Evolved Universal Terrestrial Radio Access Network) cell;
- means for generating a message for a neighboring cell of a different Radio Access Technology (RAT), another RAT, the message including at least one handover and/or cell reselection parameter for use in determining new handover and/or cell reselection parameters for the neighboring cell of the other RAT; and
- means for sending the message to a base station operating the cell of the other RAT.

13. A base station of a non E-UTRAN (Evolved Universal Terrestrial Radio Access Network) cell comprising:
- transmission circuitry for transmitting handover and/or cell reselection parameters for use by mobile communications devices to control signal measurements performed thereby as part of a handover and/or cell reselection process;
- receiving circuitry for receiving a message from an E-UTRAN communications node, the message including at least one handover and/or cell reselection parameter for use in determining new handover and/or cell reselection parameters for the non E-UTRAN cell wherein the base station is operable to determine, from said at least one handover and/or cell reselection parameter, said new handover and/or cell reselection parameters for the non E-UTRAN cell; and
- wherein said transmission circuitry is operable to broadcast the new cell selection parameters into the non-E-UTRAN cell.

14. The base station of the non E-UTRAN cell according to claim 13, wherein said circuitry is formed by software modules running on a programmable processor.

15. A communications system comprising:
- a mobile communications device, an E-UTRAN (Evolved Universal Terrestrial Radio Access Network) communications system and a non-E-UTRAN communications system,
- wherein a communications node of the E-UTRAN communications system is operable:
  - to change handover and/or cell reselection parameters of the E-UTRAN cell;
  - to provide a message for a neighboring cell of a different Radio Access Technology, RAT, the message including at least one handover and/or cell reselection parameter for use in determining new handover and/or cell reselection parameters for the neighboring cell of the non E-UTRAN cell; and
  - to send the message to a base station operating the non E-UTRAN cell,
- wherein the mobile communications device is operable to make signal measurements in accordance with handover and/or cell reselection parameters transmitted by a serving cell,
- wherein the base station operating the non E-UTRAN cell comprises:
  - transmission circuitry for transmitting handover and/or cell reselection parameters for use by mobile communications devices to control signal measurements performed thereby as part of a handover and/or cell reselection process;
  - receiving circuitry for receiving the message from the communications node of the E-UTRAN communications system, the message including at least one handover and/or cell reselection parameter for use in determining new handover and/or cell reselection parameters for the non E-UTRAN cell, wherein the base station is operable to determine, from said at least one handover and/or cell reselection parameter, said new handover and/or cell reselection parameters for the non E-UTRAN cell,
- wherein said transmission circuitry is operable to transmit the new handover and/or cell reselection parameters into the non-E-UTRAN cell, and
- wherein the mobile communications device is operable to select a cell for handover and/or cell reselection in accordance with the changed handover and/or cell reselection parameters for the E-UTRAN cell and the new handover and/or cell reselection parameters for the non-E-UTRAN cell.

16. A non-transitory computer readable medium comprising computer implementable instructions for causing a programmable computer device to perform the method of claim 1.

17. A non-transitory computer readable medium comprising computer implementable instructions for causing a programmable computer device to perform the method of claim 8.

18. The method according to claim 2, performed by a E-UTRAN cell.

19. The method according to claim 2, wherein said changing changes the threshold values transmitted by the cell that are used by mobile communications devices to control measurements performed by the mobile communications devices as part of a handover or cell reselection process.

20. A mobile communications device of the communications system according to claim 15, the mobile communications device comprising:
- means for making signal measurements in accordance with handover and/or cell reselection parameters transmitted by a serving cell; and
- means for selecting a cell for handover and/or cell reselection in accordance with the changed handover and/or cell reselection parameters for the E-UTRAN cell and the new handover and/or cell reselection parameters for the non-E-UTRAN cell.

* * * * *